United States Patent [19]

Buzas et al.

[11] 4,127,666
[45] Nov. 28, 1978

[54] DISUBSTITUTED 2,5-BENZAMIDES AND PHARMACEUTICAL COMPOSITIONS CONTAINING THE SAME

[75] Inventors: André Buzas, Bievres; Gilbert Lavielle, Orleans, both of France

[73] Assignee: Universite d'Orleans, Orleans-la-Source, France

[21] Appl. No.: 768,893

[22] Filed: Feb. 15, 1977

[30] Foreign Application Priority Data

Feb. 26, 1976 [FR] France .................. 76 05372

[51] Int. Cl.² .................. A61K 31/40; A61K 31/445; C07D 207/02
[52] U.S. Cl. .................. 424/274; 424/267; 260/326.47; 546/226
[58] Field of Search ........ 260/268 C, 268 BC, 293.77, 260/326.47; 424/274, 267

Primary Examiner—Jose Tovar
Attorney, Agent, or Firm—Young & Thompson

[57] ABSTRACT

The disubstituted 2,5-benzamides correspond to the following general formula:

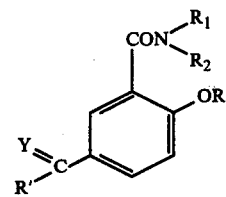

where R is an alkyl group (possessing 1 to 5 carbon atom) or an allyl group,

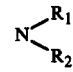

represents one of the following groups: phenylpiperazine, benzylpiperazine, piperonylpiperazine, dimethylaminoethylamino, diethylaminoethylamino, pyrrolidinyl-1 substituted methylamino, morpholine or piperidine, R' is an alkyl possessing 1 to 8 carbon atoms, a phenyl, or substituted phenyl, an alpha-aminomethyl or acrylic group, Y is an oxygen atom, an oxime, oxime ether, oxime ester or imine group.

6 Claims, No Drawings

DISUBSTITUTED 2,5-BENZAMIDES AND PHARMACEUTICAL COMPOSITIONS CONTAINING THE SAME

This invention relates to novel disubstituted 2,5-benzamides and to the applications of the derivatives aforesaid, especially in human and veterinary therapeutics.

A certain number of substituted benzamides are already known have pharmacological properties and, in particular, benzamides which correspond to the following general formula:

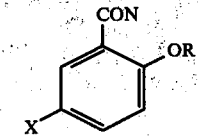

where
R is a lower alkyl radical and
where X is an attracting group such as $SO_2NH_2$; $SO_2N(R)_2$, $CF_3$ or an atome of halogen.

Metoclopramide is also known and corresponds to the formula:

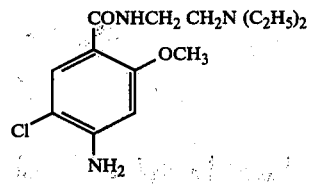

This compound has anti-emetic properties but produces as a side effect a sedative action which induces somnolence. It is apparent that a side effect of this type constitutes an appreciable disadvantage in many cases.

The use of this compound as a medicament is consequently limited essentially to that of a modifier of the digestive tract.

The aim of the present invention is to provide novel disubstituted 2,5-benzamides having distinctly more advantageous pharmacological properties than the benzamides specified in the foregoing.

In accordance with the invention, the disubstituted 2,5-benzamides are characterized in that they correspond to the general formula:

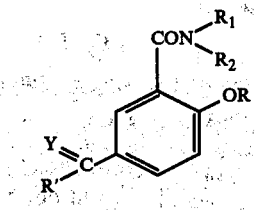

where:
R is an alkyl group (possessing 1 to 5 carbon atoms) or an allyl group.

represents one of the following groups: phenylpiperazine, benzylpiperazine, piperonylpiperazine, dimethylaminoethylamino, diethylaminoethylamino, methylamino 1-substituted pyrrolidinyl, morpholine, piperidine, R' is an alkyl group possessing 1 to 8 carbon atoms, phenyl, substituted phenyl, alpha-aminoethyl or acrylic group, Y is an oxygen atom, an oxime group, oxime ether, oxime ester or imine group.

The benzamides in accordance with the invention are preferably as follows:

N(1-ethyl-2-pyrrolidinyl-methyl)butanoyl-5-methoxy-2-beneamide, 1-piperonyl, 4(2'-methoxy,5'-butanoyl-benzoyl) piperazine, N(2-diethylaminoethyl) butanoyl-5-methoxy-2-benzamide, N(2-diethylaminoethyl) hexanoyl-5-methoxy-2-benzamide, N(2-diethylaminoethyl) benzoyl-5-methoxy-2-benzamide, N(1-ethylpyrrodinylmethyl)5(methylene-2)butanoyl-2-methoxybenzoate of methyl, N[5(piperidino-methyl-2) butanoyl, 2-methoxy-benzoyl]piperidine, N(2-dimethylaminoethyl)5(2-piperonylpiperazinomethyl)butanoyl-2-methoxy-benzamide, N(2-dimethylaminoethyl)5(1-hydroxyimino) butyl-2-methoxybenzamide, N(1-ethyl 2-pyrrolidinyl-methyl) acetyl-5-methoxy-2-benzamide.

The invention is also concerned with the pharmaceutically acceptable acid salts of benzamides in accordance with the invention, in particular the hydrochlorates, iodomethylates and maleates of these derivatives, the hydrochlorates being usually preferred.

The physico-chemical properties of the benzamides in accordance with the invention will be indicated in the examples of application of the method for producing compounds in accordance with the invention.

A first version of the method for producing compounds in accordance with the invention consists in preparing the benzamide corresponding to the general formula given above, where Y is an oxygen atom, namely as follows:

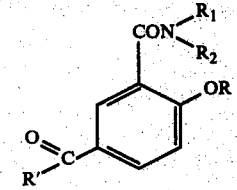

starting from a synthesis intermediate, namely the corresponding acid chloride (II) which is reacted with a suitable amine (III) in accordance with the following diagram:

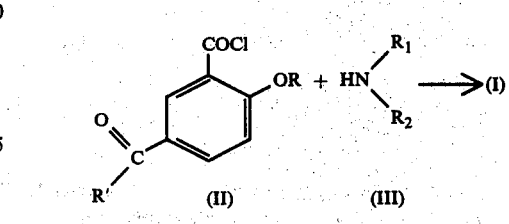

where R, R$_1$, R$_2$ and R comply with the definitions mentioned earlier. The acid chlorides (II) are in turn prepared in accordance with the following reaction diagram:

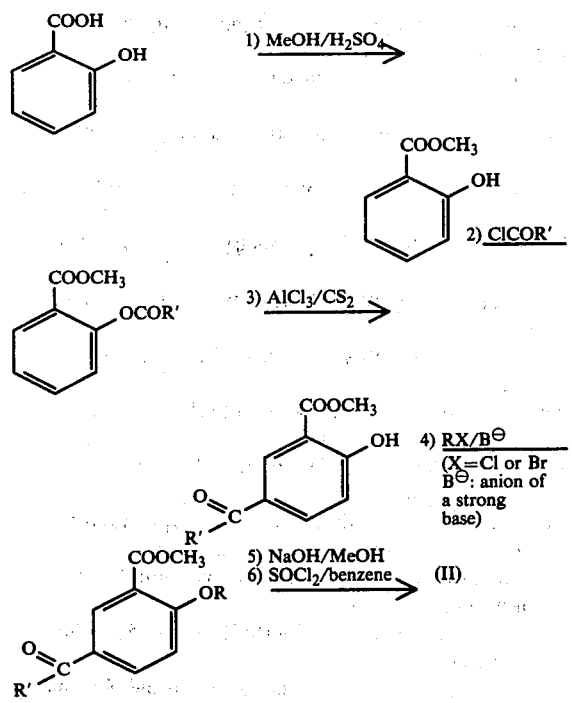

In another version of the method in accordance with the invention, in order to prepare the benzamides which correspond to formula (I) given above, the amine (III) is reacted directly with the ester:

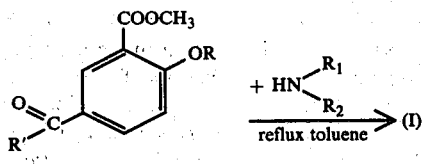

Starting from the benzamides of formula (I), the corresponding alcohols are obtained by conventional hydrogenation.

In order to prepare the benzamides in accordance with the invention, where Y is a group consisting of oxime, ether or oxime ester or imine, there is employed as starting product a benzamide corresponding to the general formula (I) aforesaid in which Y is an oxygen atom and the ketone function of said benzamide is converted in accordance with the following reactions:

1) (I) + NH$_2$OH $\longrightarrow$

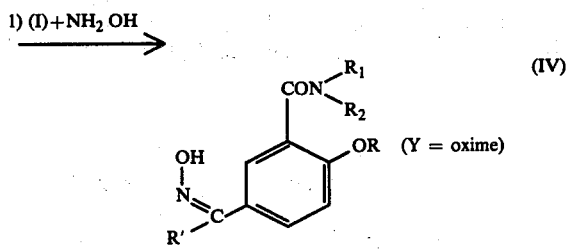

(2) Starting from benzamide (IV), the oxime ethers and esters are prepared in the standard manner.

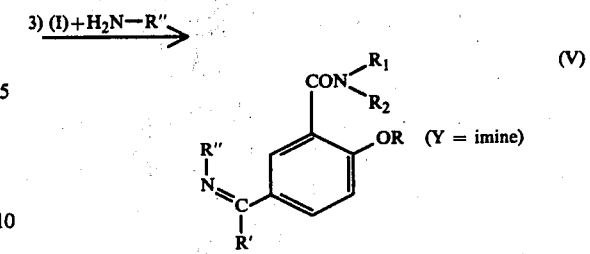

where R″ designates an alkyl radical.

By reduction of the imines (V), it is possible to prepare the corresponding amines.

(4) As result of a Mannich reaction, it is possible to convert (I) into an aminomethyl derivative of type VI.

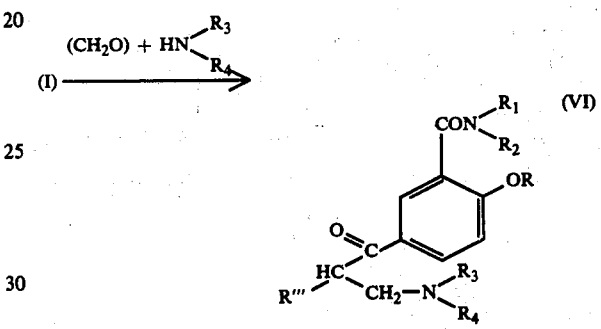

where R‴, R$_3$ and R$_4$ designate alkyl radicals.

(5) As a result of heating in an acid medium, the banzamide (VI) loses one molecule of amine and leads to VII.

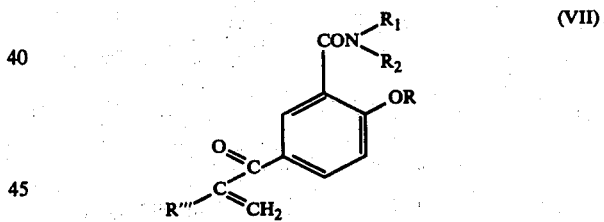

There are given hereunder a few non-limitative examples of preparation of benzamides in accordance with the invention.

EXAMPLE 1

Preparation of 2-butanoyloxy-methylbenzoate

In a 4-liter flask having a triple tube, there are placed 3 moles of methyl salycilate (456 g), 3 moles of triethylamine (420 ml) and 2 liters of CH$_2$Cl$_2$. After reaction of the mixture, cooling is carried out by means of an ice bath, 3 moles of butyryl chloride (320 g) are added with care and stirring is carried out during the night.

Distillation is performed so as to obtain, with a yield of 76%, 505 g of product having a boiling point equal to 118° C. at 0.4 bar.

EXAMPLE 2

Preparation of 5-butanoyl-2-hydroxy-methylbenzoate

The operation is performed in accordance with the general mode of preparation by E. H. Cox in J.A.C.S.

352, 52, 1930. In a 4-liter flask having a triple tube, there are dissolved 4 moles of AlCl$_3$ (532 g) in 2 liters of nitrogen. There are added 2 moles of the diester of Example 1 (444 g) in 1 hour without cooling, whereupon heating is carried out for 5 hours at 55° C.

By recrystallization of the crude mass obtained in the cyclohexane, there are obtained with a yield of 74%, 325 g of product having a melting point of 70° C. The absorption spectrum in the infrared region with KBr exhibits a wide band at 1680 cm$^{-1}$ which is characteristic of the CO group and a band of 3220 cm$^{-1}$ corresponding to OH.

EXAMPLE 3

Preparation of 5-butanoyl-2-methoxy-methylbenzoate

In a 6-liter flask having a triple tube, there are introduced 4 liters of acetone and 1 mole of ester obtained in accordance with Example 2 (222 g). There are added 2 moles of K$_2$CO$_3$ (276 g), then 1.5 mole of dimethylsuphate (190 g). Reflux heating is performed for 7 hours followed by filtration and concentration to dryness. The crude mass obtained is crystallized. There are thus obtained, with a yield of 93%, 220 g of product which melts at 72° C. IR spectrum (KBr) CO: 1670 and 1730 cm$^{-1}$.

EXAMPLE 4

Preparation of 5-butanoyl-2-methoxybenzoic acid

In a 2-liter flask having a triple tube, there are introduced 1.12 mole of NaOH (45 g), 900 ml of water, 200 ml of ethanol and 0.931 mole of the ester obtained in accordance with Example 3 (220 g). Heating is carried out for 3 hours at 80° C. After having driven out the alcohol in a vacuum, the cake is acidified, filtered and carefully washed. There are thus obtained, with a yield of 100%, 206 g of a product which melts at 105°–106° C.

IR spectrum (KBr) CO: 1670 and 1730 cm$^{-1}$ OH: 3200 cm$^{-1}$ (broad band).

EXAMPLE 5

Preparation of 5-butanoyl-2-methoxybenzoyl chloride 206 g of the acid obtained in Example 4 (0.927 mole), 1 liter of CHCl$_2$, are introduced into a triple-tube flask and 1.11 mole of SOCl$_2$ (80 ml) are added with care. The mixture is maintained for 24 hours at 30° C. and the solvents are then removed. Retreatment with 200 ml of benzene is carried out three times by removing the solvent in vacuo each time. 200 g of the product having a melting point of 65° C. (cyclohexane) are thus obtained with a yield of 90%. IR spectrum (KBr) CO: 1670 and 1780 cm$^{-1}$.

EXAMPLE 6

Preparation of the hydrochlorate of N(1-ethyl-2-pyrrolidinyl-methyl) 5-butanoyl-2-methoxybenzamide 162 g of the chloride obtained in accordance with Example 5 (0.675 mole) are dissolved in 1 liter of benzene. This is carefully introduced at a temperature below 10° C. into a mixture of 0.675 mole of triethylamine (95 ml) and 87 g of 1-ethyl-2-aminomethylpyrrolidine (0.675 mole) in 300 ml of benzene. Stirring is carried out for 12 hours followed by filtration and washing with acid water. Alkalization is then carried out followed by further extraction, whereupon the residue (180 g) is washed on 900 g of alumina by employing CH$_2$Cl$_2$ as eluent. 15 g of product are thus obtained with a yield of 70%. This base is converted to hydrochlorate in an ether-acetone mixture. There are thus obtained 150 g (dry weight) of a product having a melting point (instantaneous) which is equal to 125° C.

IR spectrum (KBr) CO: 1850 and 1690 cm$^{-1}$ (narrow band) NH: 3350 cm$^{-1}$ (narrow band)

Elementary analysis: C$_{19}$H$_{28}$N$_2$O$_3$.HCl. Calculated (%): C = 62.94; H = 7.65; N = 7.59. Found (%): C = 62.85; H = 7.75; N = 7.72.

EXAMPLE 7

Preparation of the hydrochlorate of N(piperonylpiperazine)-5-butanoyl-2-methoxybenzamide There are added 12 g of the acid chloride of Example 5 (0.05 mole) in a mixture of 11 g of piperonylpiperazine (0.05 mole) and 0.05 mole of triethylamine in CH$_2$Cl$_2$. After the reaction, the product is converted to hydrochlorate in an ethanol-acetone mixture. A product which melts at 202° C. is thus obtained with a yield of 83%.

Elementary analysis: C$_{24}$H$_{28}$N$_2$O$_5$.HCl. Calculated (%): C = 62.4; H = 6.29; N = 6.08. Found (%): C = 62.2; H = 6.18; N = 5.92.

EXAMPLE 8

Preparation of the hydrochlorate of N(2-diethylaminoethyl)-5-butanoyl-2-methoxybenzamide In a flask equipped with a Dean-Stark device, there are introduced 10 g of the ester obtained in Example 3 and 10 g of diethylaminoethylamine and the mixture is heated to 100° C. for 3 hours. There are thus obtained 10.3 g of an oily product which is converted to hydrochlorate in the ethanol-ether mixture. The product obtained has a melting point of 155° C.

Elementary analysis: C$_{18}$H$_{18}$N$_2$O$_3$.HCl. Calculated (%): C = 60.6; H = 8.13; N = 7.85. Found (%): C = 60.7; H = 8.05; N = 7.83.

EXAMPLE 9

Preparation of the hydrochlorate of N(2-diethylaminoethyl)-5-hexanoyl-2-methoxybenzamide The 5-hexanoyl-2-methoxy-methylbenzoate is prepared in accordance with the mode of operation described in the foregoing Examples 1, 2 and 3. There are obtained 26.6 g of ester which is treated with 11.6 g of diethylaminoethylamine as in Example 8. The product is converted to hydrochlorate as described earlier so as to obtain 11 g of salt which has a melting point of 144° C.

IR spectrum (KBr) - CO: 1650 and 1580 cm$^{-1}$ NH: 3380 cm$^{-1}$

Elementary analysis: C$_{20}$H$_{32}$N$_2$O$_3$.HCl. Calculated (%): C = 62.4; H = 8.58; N = 7.28. Found (%): C = 62.3; H = 8.72; N = 7.43.

EXAMPLE 10

Preparation of 5-benzoyl-2-hydroxy-methylbenzoate

The mode of operation is carried out as described in Example 2 by making use of 60 g of 2-benzoyloxy-methylbenzoate, 50 g of AlCl$_3$ and 400 ml of carbon sulphide. There are thus obtained 25 g of a crystalline product having a melting point of 95° C.

EXAMPLE 11

Preparation of 5-benzoyl-2-methoxy-methylbenzoate

The mode of operation described in Example 3 is applied to the ester obtained in Example 10. The product obtained has a melting point of 75° C.

EXAMPLE 12

Preparation of the hydrochlorate of N(2-diethyl aminoethyl)-5-benzoyl-2-methoxybenzamide The operation is performed as in Example 6 on 7 g of the chloride of 5-benzoyl-2-methoxybenzoyl. The hydrochlorate is formed as described earlier so as to obtain 9 g of salt having a melting point of 135° C.

IR spectrum (KBr) - NH: 3380 cm$^{-1}$ CO: 1850 and 1640 cm$^{-1}$

Elementary analysis: $C_{21}H_{26}N_2O_3.HCl$. Calculated (%): C = 64.5; H = 6.66; N = 7.18. Found (%): C = 64.3; H = 6.72; N = 6.93.

EXAMPLE 13

Preparation of the iodomethylate of 5(dimethylaminomethyl-2)-butanoyl-2-methoxy-methylbenzoate In a 4-liter flask having a triple tube, there are placed 127 g of the corresponding methylbenzoate obtained in accordance with Example 3, 500 ml of absolute alcohol and 53 g of dimethylamine hydrochlorate. 50 g of trioxymethylene are added at intervals of 6 hours and reflux heating is carried out for a period of 24 hours. This is followed by evaporation and retreatment with acidulated water from which is extracted 54 g of a neutral fraction. The aqueous phase is alkalized and extracted with $CH_2Cl_2$. After evaporation of the solvent, there are then obtained 74 g of an oily product which is converted directly to iodomethylate as a result of the action of $ICH_3$ (44 g) in acetone. After filtration, there are obtained 100 g of a product having a melting point of 23° C.

EXAMPLE 14

Preparation of 5(methylene-2)-butanoyl-2-methoxymethylbenzoate

In a 2-liter flask having a triple tube, there are placed 20 g of sodium hydroxide, 400 ml of water and 120 g of iodomethylate in accordance with Example 13. Reflux heating is carried out for 3 hours. 50 g of ester are thus obtained.

EXAMPLE 15

Preparation of the hydrochlorate of N(1-ethyl-2-pyrrolidinyl-methyl)-5-(methylene-2)butanoyl-2-methoxy-methylbenzoate 5.1 g of 1-ethyl-2-aminomethylpyrrolidine are reacted with 10 g of the chloride prepared from the ester of Example 14 in accordance with the mode of operation of Example 6. There are thus obtained 8 g of hydrochlorate having a melting point of 82° C.

IR spectrum (KBr) - NH: 3380 cm$^{-1}$ CO: 1680–1850 cm$^{-1}$

Elementary analysis: $C_{20}H_{28}N_2O_3.HCl$. Calculated (%): C = 63; H = 7.62; N = 7.36. Found (%): C = 62.8; H = 7.68; N = 7.14.

EXAMPLE 16

Preparation of the maleate of N-piperidine-5 (N-piperidine-methyl-2) butanoyl-2-methoxy-benzamide 14.2 g of piperidine in 50 ml of $CH_2Cl_2$ are added to 14 g of the chloride prepared from the ester of Example 14. Stirring is carried out during the night at room temperature. After removal of the neutral fractions, 12 g of oily product are recovered and converted directly to maleate. There are obtained 11 g of product having a melting point of 170° C.

Elementary analysis: $C_{23}H_{34}N_2O_3.C_4H_4O_4$. Calculated (%): C = 63.55; H = 7.57; N = 5.56. Found (%): C = 63.4; H = 7.43; N = 5.38.

EXAMPLE 17

Preparation of the trimaleate of N(2-dimethylaminoethyl)-5-(2-piperonylpiperazino-methyl)-butanoyl-5-methoxy-benzamide 1.3 g of piperonylpiperazine in 100 ml of benzene are added to 1.7 g of N(2-dimethylaminoethyl)-5-(methylene-2) butanoyl-2-methoxy-benzamide. After reflux heating for 5 hours, the benzene is removed, there being then carried out a conversion to trimaleate in alcohol. 2.5 g of product having a melting point of 134° C. are obtained.

Elementary analysis: $C_{31}H_{44}N_4O_5.3C_4H_4O_4$. Calculated (%): C = 57.4; H = 6.23; N = 6.23. Found (%): C = 57.3; H = 6.15; N = 5.93.

EXAMPLE 18

Preparation of the hydrochlorate of N(2-dimethylaminoethyl)-5-(1-hydroxyimino)-butyl-2-methoxy-benzamide.

In a 500 ml flask having a triple tube, 14.6 g of hydroxylamine hydrochlorate are dissolved in 60 ml of water. There are added 22.4 g (0.07 mole) of the benzamide of Example 8 in 100 ml of ethanol. A solution of 5.6 g of sodium hydroxide in pellets (0.14 mole) is then carefully introduced in 60 ml of water, whereupon the mixture is heated and refluxed for a period of 8 hours.

After recrystallization in isopropyl ether, 18 g of product having a melting point of 88° C. are obtained and converted to hydrochloride which melts at 124° C.

Elementary analysis: $C_{18}H_{29}N_3O_3.HCl$. Calculated (%): C = 58.1; H = 8.07; N = 11.3. Found (%): C = 57.9; H = 8.13; N = 11.5.

EXAMPLE 19

Preparation of 5-butanoyl-2-allyloxy-methylbenzoate

In a 500 ml flask having a triple tube, there is prepared a solution of ethylate with 4.6 g of Na in 120 ml of ethanol. There are then added in the cold state 45 g (0.2 mole) of the methyl benzoate of Example 2 followed by 29 g (0.24 mole) of allyl bromide, heating and refluxing being then carried out for a period of 20 hours.

After recrystallization in isopropyl ether, 40 g of product having a melting point of 55° C. are obtained.

EXAMPLE 20

Preparation of the hydrochlorate of N(2-diethylaminoethyl)-5-butanoyl-2-allyloxy-benzamide The ester of Example 19 is treated in accordance with the same mode of operation as that described in Example 8. The product thus obtained has a melting point of 112° C.

Elementary analysis: $C_{20}H_{30}O_3N_2.HCl$. Calculated (%): C = 62.7; H = 8.11; N = 7.32. Found (%): C = 62.5; H = 7.93; N = 7.15.

EXAMPLE 21

Preparation of the hydrochlorate of N(2-diethylaminoethyl)-5-acetyl-2-methoxy-benzamide The operation is carried out as in Example 8 starting from 5-acetyl-2-methoxy-methylbenzoate. There is thus obtained a product having a melting point of 183° C.

Elementary analysis: $C_{16}H_{26}O_3N_2.HCl$. Calculated (%): C = 58.2; H = 7.62; N = 8.53. Found (%): C = 57.9; H = 7.48; N = 8.47.

EXAMPLE 22

Preparation of the hydrochlorate of N(2-diethylaminoethyl)-5-(butanol-1)-2-methoxy-benzamide 9.6 g of the benzamide of Example 8 are dissolved in methanol. After cooling, 9 g of sodium borohydride are added in portions and stirring is effected for 1 hour. There is thus obtained an oily product which is converted to hydrochlorate. The product obtained has a melting point of 122° C.

Analysis: $C_{18}H_{20}N_2O_3.HCl$. Calculated (%): C = 60.2; H = 5.85; N = 7.8. Found (%): C = 59.8; H = 5.72; N = 7.6.

EXAMPLE 23

Preparation of the hydrochlorate of N(1-ethyl-2-pyrrolidinylmethyl)-5-acetyl-2-methoxy benzamide (a) Preparation of acetyl-5-hydroxy-2-methyl benzoate In a 2 l flask having a triple tube are introduced 1 200 ml of $CH_2Cl_2$, 267 g of anhydrous $AlCl_3$ (2 moles). The mixture is agitated during 1 hour at about 25° C. Then are added 152,1 g of methyl salicylate (1 mole). The temperature is maintained at 25° C. HCl evolves during addition of the methyl salicylate. Then are added at 25° C. during 1 hour 118 g (108 ml, 1,5 mole) acetyl chloride. An homogenous mass precipitates slowly. The agitation is maintained during one night at normal temperature.

The reaction medium is then added to a mixture of ice (1 kg) and concentrated HCl (200 ml) the mixture is then decanted and washed with 2 × 500 ml of water and then dried on $SO_4Na_2$. The solvant is then evaporated. The product is recristallized in cyclohexane (300 g). The weight of the obtained product is 174.2 g, melting point: 61° C., yield: 90%.

(b) Preparation of acetyl-5-methoxy-2-methyl-benzoate

In a 2 l flask having an agitator and a vertical refrigerant, are introduced:

77.7 g (0.4 mole) of the compound (a)
800 ml acetone.

The mixture is agitated up to complete dissolution and then are added: 75.7 g (0.6 mole) of dimethyl sulfate and 110.6 g (0.8 mole) of $CO_3K_2$. The mixture is heated at reflux for 7 hours. The obtained mass is treated with isopropylic ether and then crystallized and filtered. 79 g of a dry product which melts at 95° C. is thus obtained. Yield 95%.

(c) Preparation of acetyl-5-methoxy-2-benzoic acid

See example 4. The obtained product melts at 154° C. Yield: 95%.

(d) Preparation of acetyl-5-methoxy-2-benzoic chloride.

See example 5. The obtained product melts at 69°-70° C.

(e) Preparation of the hydrochlorate of N(1-ethyl-2-pyrrolidinyl methyl)-5-acetyl-2-methoxy benzamide The method is similar to that of example 6, using the chloride (d). The obtained product has the following characteristics:

Melting point: 154° C.

IR spectrum (KBr): NH: 3320 $cm^{-1}$ (narrow band) CO: 1680 $cm^{-1}$-1640 $cm^{-1}$.

Elementary analysis: $C_{17}H_{24}N_2O_3$ HCl Calculated (%): C = 59.84; H = 7.04; N = 8.21. Found (%): C = 60.17; H = 6.98; N = 8.13.

The invention is also concerned with the application in human and veterinary therapeutics of the benzamides in accordance with the invention and of their pharmaceutically acceptable salts, especially the hydrochlorates.

The results of pharmacological tests carried out on the benzamides in accordance with the invention are given hereunder.

(1) Toxicity

The toxicity has been established perorally in the male Swiss mouse.

The lethal doses 50 in the case of benzamides prepared in accordance with the different examples given above are the following:

| Example | |
|---|---|
| " | 6 = 350 mg/kg |
| " | 7 = 800 |
| " | 8 = 600 |
| " | 9 = 650 |
| " | 12 = 250 |
| " | 15 = 800 |
| " | 16 = 800 |
| " | 17 = <1600 |
| " | 18 = 500 |
| " | 20 = 275 |
| " | 21 = 600 |
| " | 23 = 325 |

(2) Reduction of motor activity

It has been endeavoured to determine this property in the Swiss mouse in a free situation. Actimetric measurements have served to calculate the DE 50 doses of each substance administered perorally.

The peroral DE 50 doses in mg/kg which have been obtained are as follows:

| Example | |
|---|---|
| " | 6 = 40±5 |
| " | 7 = >100 |
| " | 8 = >100 |
| " | 9 = >100 |
| " | 12 = >50 |
| " | 15 = 0 |
| " | 16 = 0 |
| " | 17 = 0 |
| " | 18 = 100±12 |
| " | 20 = >50 |
| " | 21 = 45±5.5 |
| " | 23 = 5±0.75 |

(3) Potentialization of barbituric narcosis

It has been sought to determine the potentialization of a liminary dose of nembutal in the Swiss mouse.

The effective doses 50 have been determined after oral administration of the benzamides in accordance with the invention.

The peroral DE 50 doses in mg/kg obtained are as follows:

| Example | |
|---|---|
| 6 | = >100 |
| 7 | = 100 |
| 8 | = 100 |
| 9 | = >100 |
| 12 | = 75 |
| 15 | = >100 |
| 16 | = 200 |
| 17 | = >400 |
| 18 | = 50 |
| 20 | = >50 |
| 21 | = 100 |
| 23 | = 100 |

(4) Anti-emetic properties (a) Apomorphine test performed on dogs

The compounds are administered subcutaneously in an aqueous solution in Beagles dogs 30 minutes prior to subcutaneous administration of a dose of 100 microgrammes/Kg of apomorphine.

| Example | Doses administered in mg/kg | % reduction in vomiting frequency |
|---|---|---|
| 6 | 0.100 | 100 |
| 7 | 0.500 | 0 |
| 8 | 0.500 | 100 |
| 9 | 1 | 0 |
| 12 | 1 | 0 |
| 15 | 2 | 50 |
| 16 | 1 | 0 |
| 17 | 1 | 0 |
| 18 | 0.500 | 0 |
| 20 | 0.500 | 50 |
| 21 | 0.125 | 50 |
| 23 | 0.050 | 100 |

In the case of the benzamide of Example 6, the DE 50 does is 0.050 mg/kg administered subcutaneously. In the case of the benzamide of Example 8, the DE 50 does is 0.210 mg/kg administered subcutaneously. For the benzamide of Example 23, the DE 50 dose is 0.006 mg/kg administered subcutaneously.

The same test was performed in the case of the benzamide of Example 6 by administering this compound perorally in Beagles 1 hour prior to subcutaneous administration of a dose of microgramme/kg of apomorphine.

The results obtained are as follows:

| Dose administered perorally in mg/kg | % reduction in vomiting frequency |
|---|---|
| 0.500 | 100 |
| 0.250 | 66.7 |
| 0.100 | 30.8 |

The DE 50 dose obtained in the case of the benzamide of Example 6 is 0.250 mg/kg administered perorally.

The same test has been performed with the benzamide of Example 23.

The obtained results are the follows:

| Dose administered perorally in mg/kg | % reduction in vomiting frequency |
|---|---|
| 0.050 | 100 |
| 0.025 | 80 |
| 0.0125 | 54 |
| 0.0100 | 33 |

The DE 50 obtained in the case of the benzamide of Example 23 is 0.013 mg/kg administered perorally.

(b) Hydergine test performed on dogs

Hydergine injected intravenously at a dose of 90 microgrammes/kg induces vomiting in dogs and the antiemetics are capable of inhibiting such vomiting. The benzamides are administered subcutaneously 30 minutes prior to the hydergine.

The results obtained in the case of the benzamide of Example 6 are given hereunder.

| Dose administered subcutaneously in mg/kg | reduction in vomiting frequency |
|---|---|
| 0.500 | 100 |
| 0.250 | 100 |
| 0.125 | 80 |
| 0.050 | 54.5 |
| 0.025 | 37.5 |

The DE 50 dose obtained is 0.040 mg/kg administered subcutaneously.

The result obtained in the case of the benzamide of Example 23 are given herunder:

| Dose administered subcutaneously in mg/kg | % reduction in vomiting frequency |
|---|---|
| 0.050 | 100 |
| 0.025 | 100 |
| 0.0125 | 37.5 |
| 0.00625 | 0 |

(c) Copper sulphate test

The copper sulphate administered to dogs perorally induces vomiting during the hour which follows ingestion of this product.

The benzamide is administered perorally one hour prior to the copper sulphate.

The results obtained in the case of the benzamide of Example 6 are given hereunder:

| Peroral doses in mg/kg | % reduction in vomiting frequency |
|---|---|
| 0.500 | 100 |
| 0.250 | 40 |
| 0.125 | 20 |

The DE 50 dose in the case of this benzamide is 0.300 mg/kg administered perorally.

The results of the foregoing pharmacological tests clearly show that the benzamides in accordance with the invention have powerful anti-emetic properties with respect to the various central emesis-inducing agents such as apomorphine and hydergine and peripheral emesis-inducing agents such as copper sulphate.

In this connection, the most active product is the benzamide of Example 23 (hydrochlorate of N(1-ethyl-2-pyrrolidinyl-methyl)-5-acetyl-methoxy-2 benzamide).

Furthermore, the benzamides in accordance with the invention are remarkable by reason of the fact that their depressive activity on the central nervous system is very low with respect to their anti-emetic activity.

Thus the benzamide in accordance with Example 6 depresses the motor activity of mice by 50% at doses 80 times higher than those which provide total protection against apomorphine emesis.

That of Example 23 depresses the motor activity of mice by 50% at doses 100 times higher than of the antiemetic doses.

Moreover, a further advantage of these benzamides is that they do not potentialize barbiturates.

The medicament containing substituted benzamide as an active substance in accordance with the invention is consequently suitable for the treatment of vomiting of all types such as vomiting caused by hepato-digestive disorders, common vomiting of nursing infants, vomiting and nausea caused by intolerance to medicines, vomiting and nausea caused by anesthetics, by gastric tubes and by digestive endoscopies.

For the treatment of these ailments, the medicaments which contain by way of active substance a benzamide in accordance with the invention can be administered in the form of solutions by intramuscular injections, drops, gelules, compressed tablets or suppositories.

The preferential dosology is as follows:

oral administration: 5 to 15 mg of active substance per diem parenteral administration: 1 to 5 mg of active substance per diem rectal administration: 2.5 to 10 mg of active substance per diem.

A few examples of pharmaceutical forms of the medicament in accordance with the invention are given hereunder.

| Gelule : | |
|---|---|
| Active substance (benzamide in accordance with Example 6 or 23) | 5 mg |
| Lactose | 20 mg |
| Compressed tablet : | |
| Benzamide in accordance with Example 6 or 23 | 5 mg |
| Talc and starch as excipient for compression | 20 mg |
| Suppository : | |
| Benzamide in accordance with Example 6 or 23 | 2.5 mg |
| Suppository wax C | q.s. 1 g |
| Injectable ampoule : | |
| Benzamide in accordance with Example 6 or 23 | 1 mg |
| Double-distilled water | 2 ml. |

What we claim is:

1. A disubstituted 2,5 benzamide having the formula

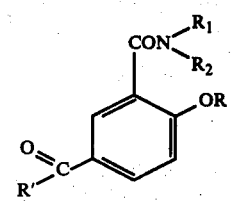

where
R is a $C_{1-5}$ alkyl group,
$R_1$ and $R_2$, together with the nitrogen atom form a piperidino group, or $R_1$ is hydrogen and $R_2$ is the following group:

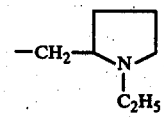

or a pharmaceutically acceptable acid addition salt, or the iodomethylate thereof.

2. Benzamide in accordance with claim 1, constituted by N(1-ethyl-2 pyrrolidinyl-methyl)-butanoyl-5-methoxy-2-benzamide.

3. Benzamide in accordance with claim 1, constituted by N(1-ethyl-2-pyrrolidinyl-methyl)acetyl-5-methoxy-2-benzamide.

4. A pharmaceutical composition for the treatment of vomiting containing as active substance a benzamido or salt according to claim 1, and a pharmaceutically acceptable diluent.

5. A pharmaceutical composition in accordance with claim 4, in which said active substance is hydrochlorate of N(1-ethyl-2-pyrrolidinyl-methyl)-butanoyl-5-methoxy-2-benzamide.

6. A pharmaceutical composition in accordance with claim 4, in which said active substance is the hydrochlorate of N(1-ethyl-2-pyrrolidinyl-methyl)-acetyl-5-methoxy-2-benzamide.

* * * * *

UNITED STATES PATENT AND TRADEMARK OFFICE
CERTIFICATE OF CORRECTION

PATENT NO. : 4,127,666
DATED : November 28, 1978
INVENTOR(S) : Andre BUZAS and Gilbert LAVIELLE It is certified that error appears in the above—identified patent and that said Letters Patent are hereby corrected as shown below:

In Item 73 of the caption, change

"Assignee: Universite d'Orleans, Orleans-la-Source, France" to

--Assignee: Universite d'Orleans, a part interest --

Signed and Sealed this

Fifteenth Day of May 1979

[SEAL]

Attest:

RUTH C. MASON
Attesting Officer

DONALD W. BANNER
Commissioner of Patents and Trademarks